United States Patent [19]
Santerre et al.

[11] Patent Number: 5,866,629
[45] Date of Patent: Feb. 2, 1999

[54] DENTAL AND MEDICAL PRIMER FORMULATIONS CONTAINING TISSUE INFILTRATING AGENTS

[75] Inventors: Paul Joseph Santerre, Whitby; Keith Titley, Toronto; Robert Chernecky, Bramalea; Phillip Watson, Don Mills, all of Canada

[73] Assignee: The University of Toronto Innovations Foundation, Toronto, Canada

[21] Appl. No.: 568,596

[22] Filed: Dec. 5, 1995

[51] Int. Cl.⁶ .................................................. A61K 6/08
[52] U.S. Cl. ............................................................ 523/118
[58] Field of Search .................................... 523/116, 118

[56] References Cited

U.S. PATENT DOCUMENTS

| | | | |
|---|---|---|---|
| 4,521,550 | 6/1985 | Bowen | 523/116 |
| 4,563,184 | 1/1986 | Korol | 604/368 |
| 4,588,756 | 5/1986 | Bowen | 523/116 |
| 4,698,376 | 10/1987 | Asmussen et al. | 523/115 |
| 4,719,149 | 1/1988 | Assen et al. | 428/473 |
| 4,810,195 | 3/1989 | Asmussen et al. | 433/215 |
| 4,952,613 | 8/1990 | Hosoda | 523/109 |
| 5,085,726 | 2/1992 | Omura et al. | 156/307.3 |
| 5,256,447 | 10/1993 | Oxman et al. | 427/207.1 |
| 5,258,067 | 11/1993 | Podszum et al. | 106/35 |
| 5,270,351 | 12/1993 | Bowen | 523/116 |
| 5,277,739 | 1/1994 | Müller et al. | 156/330.9 |
| 5,290,172 | 3/1994 | Sakuma et al. | 433/215 |
| 5,401,528 | 3/1995 | Schmidt et al. | 427/202 |
| 5,401,783 | 3/1995 | Bowen | 523/116 |
| 5,498,643 | 3/1996 | Antonucci et al. | 523/116 |
| 5,533,995 | 7/1996 | Corish et al. | 604/890.1 |

OTHER PUBLICATIONS

Titley, K. et al., "An SEM Examination of Etched Dentin and the Structure of the Hybrid Layer", *Journal of Canada Dental Association*, vol. 61, No. 10, pp. 887–894 (1995).

Titley, K. et al., "Penetration of a Dentin Bonding Agent into Dentin", *American Journal of Dentistry*, vol. 7, No. 4, pp. 190–194 (1994).

Titley, K. et al., "The Morphology of the Demineralized Layer in Primed Dentin", *American Journal of Dentistry*, vol. 7, No. 3, pp. 22–26 (1994).

*Primary Examiner*—Peter F. Kulkosky
*Attorney, Agent, or Firm*—Lahive & Cockfield, LLP; W. Hugo Liepmann, Esq.; Elizabeth A. Hanley, Esq.

[57] ABSTRACT

Tissue infiltrating primer formulations and methods of using such formulations, e.g., in the dental or medical fields, are described. The formulations of the invention include an effective amount of a tissue infiltrating agent and a primer. The tissue infiltrating primer formulations provide enhanced penetration of a biomaterial into a target substrate, e.g. hard tissues, when compared to their non-tissue infiltrating primer formulation counterparts.

12 Claims, 16 Drawing Sheets

5,866,629

DENTAL AND MEDICAL PRIMER FORMULATIONS CONTAINING TISSUE INFILTRATING AGENTS

BACKGROUND OF THE INVENTION

The use of biomaterials, e.g. restorative materials, in both the dental and medical fields is widespread and there is a high demand for products in this area. Restorative materials, e.g. amalgam or resin composites, are used extensively to repair dental tissues and bones.

In the dental field, there has been a focus on improving the adhesion of resins to hard tissue, e.g., dentin or enamel. The adhesives typically are used after pretreating or etching the hard tissue with an acid, e.g., maleic, phosphoric, or citric. New resin composites are continually being developed and marketed. Some of these composites are designed to achieve higher bond strengths or improve physical properties and esthetics of the restored target substrate. Other goals in the design of these composites are related to their use and include reducing operating time and formulating for simpler use or use under relatively humid conditions (see Titley et al. *American Journal of Dentistry,* Vol. 7, No. 4, (August 1994)).

Bonding systems typically used in the dental field remove the smear layer and demineralize the surface of the dental tissue by acid etching. The systems also can use priming agents, e.g., to alter wettability or chemical reactivity of the pretreated dentin, prior to applying a bonding agent, e.g., a polymerizable monomer. Following polymerization, the bonding agent bonds to the dentin in a manner which is not entirely understood (chemically, mechanically, interfacial diffusion or a combination thereof) by those skilled in the art. After the application of bonding systems and their polymerization, an approximately 5 micron thick hybrid layer is formed which is part resin and part dentin. This hybrid layer has been studied with an emphasis on its composition and the importance of the depth and effectiveness of the penetration of the bonding agent. (see Titley et al. *American Journal of Dentistry,* cited supra). The layer is believed to contain little or no apatite and the adhesion to dentin is believed to occur through the investment of collagen with the bonding agent. Until recently, it was difficult to study the interactions occurring in the hybrid layer because the collagen-bonding agent combinations were not clearly demonstrated.

Even though there has been focus in this area, presently available techniques and/or products for pretreating the dental tissue or adhering the restorative materials to the dental tissue have limitations. The clinical requirements of the bonds are known in that the bonding agents should effectively seal the dentin tubules to prevent post operative sensitivity and protect the pulp and the bonds should last the lifetime of the restoration and be durable under a variety of conditions. Those skilled in the art have encountered difficulties in achieving these requirements. This is partly due to the fact that the mechanism of the bonding of resin composites to the hard tissues is not entirely understood.

SUMMARY OF THE INVENTION

The present inventors have developed techniques which allow for the visualization and study of the hybrid layer in a dental tissue. The techniques allow for the visualization of the collagen-bonding agent combination in the hybrid layer and more particularly have led to a more complete understanding of how conventional bonding agents interact with the collagen matrix present in a dental tissue or tooth. The inventors were able to study the interaction between conventional bonding agents and their target substrate used in the dental field and realized that complete penetration of the treated zone of a dental tissue was not being achieved. The inventors further realized that a proper seal at the bonding agent, e.g., resin, dentin or enamel interface also was not being provided using conventional agents and techniques.

The present invention provides a means for enhancing the penetration of such treated zones using a tissue infiltrating agent(s) (TIAs). The realization and acceptance that complete penetration was not being achieved led to the development of the formulations of the present invention. The present invention pertains to tissue infiltrating primer formulations and methods of using such formulations, e.g., in the dental or medical fields. The formulations of the invention include an effective amount of a tissue infiltrating agent and a primer. The tissue infiltrating primer formulations provide enhanced penetration of a biomaterial into a target substrate when compared to their non-tissue infiltrating primer formulation counterparts.

Other aspects of the invention include dental tissues containing restorative material penetrated in an enhanced manner and packaged primer formulations. The restorative material-containing dental tissues are dental tissues containing a restorative material penetrated through a treated zone to a depth of at least about four microns. The packaged primer formulation for use with a tissue infiltrating agent is a package containing a primer formulation and instructions for using the formulation in combination with a tissue infiltrating agent. The package optionally can contain the tissue infiltrating agent.

BRIEF DESCRIPTION OF THE DRAWINGS

Designations are provided on the scanning electron micrographs of the Figures as follows: "c" denotes collagen fibres; "d" denotes dentin; "r" denotes unfilled resin; "rt" denotes resin tags; and "sm" denotes smear layer.

FIG. 2B is a top view of the etched dentin revealing the presence of the resin tags which shows no continuity of resin into the collagen matrix and further reveals the collagen matrix fibrils. The voids existing between the observed fibrils are the interstices where the mineral material previously existed prior to etching. In this case, resin did not penetrate these voids as it did when the TIA was used as shown in FIG. 2A.

FIG. 6A is the sample that was treated with TIA/primer and demonstrates the continuity of resin from the unfilled resin layer, down through the collagen and into the resin tags formed within the tubules of the dentin. By contrast, the application of one coat of primer not containing any TIA (FIG. 6B) shows complete separation of the unfilled resin layer from the collagen layer and receding of the uninfiltrated collagen layer from the sound dentin due to the lack of mechanical support resulting from the absence of a supporting resin.

DETAILED DESCRIPTION

Figure 1:
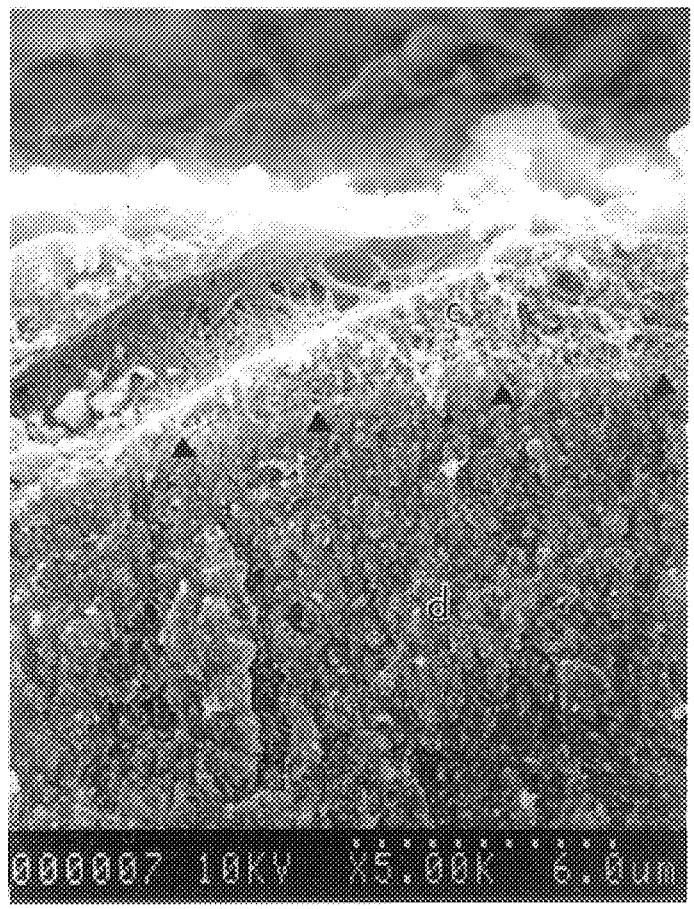
FIG. 1 shows a scanning electron micrograph (SEM) of a cross-sectional profile of dentin in a tooth treated with 35% phosphoric acid. This is a standard etchant used in the clinical application of dental adhesives. A greater portion of the original biological matrix that defines dentin is resolved by SEM as a result of using critical point drying techniques for the specimens rather than the more traditional drying methods (see Titley et al, cited supra). The top 3–4 microns of the dentin shown here reveals the fibrils of the collagen material following the etching process. At a surface depth of about 3–4 microns the presence of dense matter which is the sound dentin (i.e. collagen imbedded in hydroxy apatite) is clearly differentiated from the fibrous collagen layer. It is this collagen matrix that primer/resin adhesive systems must penetrate if successful sealing of the dentin/restorative material interface is to occur. Secondary cavity formation will occur as a result of bacterial micro-leakage into the non-continuous adhesive layer at the dentin/restorative material interface if there is not proper sealing regardless of the bond strength between the restoration and the dentin surface.

The present invention pertains to a method for preparing a primed target substrate for inclusion of a biomaterial, e.g., restorative material. The inclusion of the biomaterial can be adhesion of the biomaterial to a component of the target substrate or placement within the target substrate. The method includes contacting a target substrate with an effective amount of a tissue infiltrating agent forming a primed target substrate that is prepared for inclusion or adhesion of a biomaterial. The method further can include a step of including or adhering a biomaterial to the primed target substrate forming a biomaterial-containing target substrate.

The language "target substrate" includes substrates for which inclusion of a biomaterial would be desirable and which is amenable to penetration by a biomaterial. The target substrate can be a collagen-containing material or can be a non-collagen containing material such as porcelain or ceramic. The target substrate also may be a tissue, e.g., hard tissue (human or non-human mammal). The tissue can be a hard tissue or a soft tissue. An example of a soft tissue would be scalp, or the like. For example, the TIAs of the present invention can be used to enhance the penetration of a biomaterial into the scalp of a subject having a hair transplant.

The language "hard tissue" is art-recognized terminology. The hard tissue used within this invention is any hard tissue amenable to penetration with a biomaterial. Examples of hard tissue include dental tissue, e.g. dentin or enamel, bone, cartilage, the tissue under and/or adjacent to finger nails or toe nails, or the like. For example, the TIAs of the present invention can be used to enhance the penetration of a biomaterial used to fix artificial finger nails or toe nails onto a subject. The TIAs further can be used to enhance the penetration of a biomaterial into cartilage or bone which can be used to hold a prosthetic device in place in vivo.

The "primed target substrate" is a target substrate which has been contacted with a tissue infiltrating agent of the present invention which is defined in detail below. The tissue infiltrating agent can be applied alone or as part of a primer formulation. The agent typically is applied on the surface of the target substrate.

The term "biomaterial" is art-recognized and includes a material which typically is used in repair of or in conjunction with the target substrates of this invention. The language "restorative material" also is art-recognized and typically is used to describe a biomaterial used in the dental field. Examples of types of biomaterials include pure metals or alloys, amalgam, a ceramic composite, or a composite comprising a polymer, e.g., adhesive (or a mixture of polymers) with or without a particulate inorganic and/or organic filler. The biomaterials useful in the present invention are commercially available and include those materials which are sold as components in kits described in detail in the examples below. For ease of discussion below, the language "restorative material" will be used when describing dental applications but this should in no way be construed as limiting the invention.

The language "tissue infiltrating agent" (hereinafter "TIA") is intended to include agents which facilitate penetration of a biomaterial into a target substrate. The TIA can be administered alone or in combination with other TIAs. The TIA further can be administered alone or as a component in a primer formulation. An effective amount of the TIA is that amount required for the TIA to perform its intended function of facilitating the penetration of the biomaterial into the target substrate. The TIAs of the present invention can be obtained commercially and/or can be synthesized using art-recognized techniques.

The preferred TIAs of the present invention possess the presence of some polar character. The preferred TIAs even further may have a high dipole moment and/or dielectric constant. A dipole moment is a measure of the polarity of a single solvent molecule. A dielectric constant is a measure of the polarity of the whole solvent liquid (i.e., includes many solvent molecules and their interactions). The dielectric constant is indicative of the ability of a solvent to solvate ions which is measured by the solvent's polarity. The dielectric constants of the TIAs preferably are greater than 40, more preferably greater than 45, and most preferably greater than 49. The dipole moments of the TIAs are preferably greater than 2.00, more preferably greater than 3.00, even more preferably greater than 3.50 and most preferably greater than 3.75. Table 1 set forth below provides specific information about the characteristics of the TIAs used in the examples below.

TABLE 1

| Solvent | Dielectric Constant | Dipole Moment | Chemical Reactivity with Tissue | Molecular Weight | Van der Waals Forces | Hydrogen Bonding with Itself |
|---|---|---|---|---|---|---|
| DMSO | 49 | 3.96 | minimal | 78 | yes | no |
| DMAc | 59 | 3.76 | minimal | 87 | yes | minimal |
| DMF | 59 | 3.83 | yes | 73 | yes | strong |
| Methanol | 32 | 1.70 | minimal | 32 | yes | strong |

The TIAs of the present invention also may have a minimal degree of chemical reactivity with the target substrate, e.g., tissue. It also is desirable that the TIAs of this invention be of a relatively small size such that physical entanglement with the target substrate, e.g., tissue, or size exclusion from the target substrate is avoided or minimized.

The TIAs of the present invention also include compounds encompassed by one of the following subgenuses:

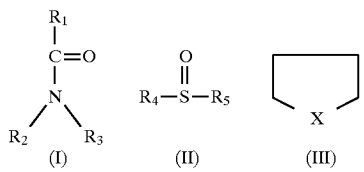

wherein $R_1$–$R_5$ are each independently selected from the group consisting of hydrogen, alkyl, alkenyl, alkynyl, alkoxyl and haloalkyl and X is selected from the group consisting of O, S and —$SO_2$—. Preferably, $R_1$ is not hydrogen in formula (I). The five membered ring of formula (III) can be substituted or unsubstituted. The substituents can include one or more alkyl, alkenyl, alkynyl, alkoxyl or haloalkyl groups as described below which can be placed at any position on the heterocyclic ring which does not detrimentally effect the TIA's ability to perform its intended function.

The alkyl, alkenyl and alkynyl groups (hereinafter hydrocarbon groups) may have straight or branched chains. The unsaturated groups may have a single site of unsaturation or a plurality of sites of unsaturation. The hydrocarbon groups preferably have up to about ten carbons, more preferably up to about six carbons, and most preferably up to about three carbons. A hydrocarbon group having three carbon atoms or less is considered to be a lower hydrocarbon group. For example, an alkyl group having three carbon atoms or less is a lower alkyl. Examples of lower hydrocarbon groups which may be used in the present invention include methyl, ethyl, ethenyl, ethynyl, propyl, propenyl, and propynyl. Examples of higher hydrocarbon groups (from four to about ten carbons) include butyl, t-butyl, butenyl, butynyl, nonyl, nonenyl, and nonynyl.

The alkoxyl and haloalkyl groups (hereinafter substituted hydrocarbon groups) are alkyl groups substituted with one or more oxygen or halogen atoms. The alkoxy and haloalkyl groups also may be straight or branched chain and preferably are made up of up to about ten atoms (including carbon, oxygen or halogen), preferably up to about six atoms, and most preferably up to about three atoms. The term halogen is art-recognized and includes chlorine, fluorine, bromine, and iodine. Examples of substituted hydrocarbon groups which are useful within this invention are similar to hydrocarbon groups set forth above except for the incorporation of oxygen(s) or halogen(s) into the groups.

Specific examples of TIAs of the present invention include dimethylsulphoxide (DMSO), dimethylacetamide (DMAc), dimethylformamide (DMF), and tetrahydrofuran (THF), N-methylpyrrolidinone, tetrahydrothiophene, 2-methyl tetrahydrofuran, 1,4-dioxane, sulfolane, and nitromethane.

The tissue infiltrating agents of the present invention also can be included in primer formulations forming a tissue infiltrating primer formulation. The tissue infiltrating primer formulations of the present invention are capable of providing enhanced penetration of a biomaterial into a target substrate when compared to their non-tissue infiltrating counterparts.

The tissue infiltrating primer formulations contain both a tissue infiltrating agent and a primer. The tissue infiltrating agents are as described above. Primers used within the formulations of the present invention can be any primer capable of being a vehicle for the selected TIA and allowing for its facilitation of penetration of a biomaterial into a target substrate. Primers are art recognized and commercially available. Examples of specific primers are those sold as components of the kits described in the examples below. The volumetric ratio of primer to TIA present in the primer formulations can vary depending upon such factors as the selected target substrate, the selected primer, and the selected TIA. Examples of volumetric ratios useful within this invention include 1:10 (primer:TIA) to and including 10:1 (primer:TIA). The more preferred volumetric ratios include 4:1 (primer:TIA) to and including 9:1 (primer:TIA). Specific tissue infiltrating primer formulations are described in detail in the examples below.

The penetration of the biomaterial into the target substrate can be measured or evaluated by those of ordinary skill in the art. For example, the tissue infiltrating primer formulation of the present invention can provide enhanced penetration of a biomaterial into a target substrate when compared to its non-tissue infiltrating primer formulation counterpart.

This is intended to include a side by side comparison of the degree of penetration of a biomaterial into a target substrate when treated with a primer formulation of the present invention compared to the same target substrate when treated with a primer formulation of the same composition but which does not contain a TIA. The degree of penetration can be observed by the ordinarily skilled artisan or measured using conventional techniques (see, e.g., Titley et al. *J Canada Dent. Assn.* 61 (10) 887–894, 1995)

The degree of penetration into a dental tissue can be evaluated based upon the distance to a barrier seal to microleakage located within the dental tissue. The tissue infiltrating primer formulations of the present invention when applied to a treated dental tissue provide a farther barrier seal to microleakage by enhancing restorative material penetration into the dental tissue when compared to the distance of a barrier seal achieved with any non-tissue infiltrating primer formulation. The non-tissue infiltrating primer formulation is intended to include primer formulation of the same composition with the tissue infiltrating agent is omitted.

Another way to compare or evaluate penetration of the biomaterial into a target substrate would be to determine the percent penetration of a biomaterial into a treated zone of a target substrate, e.g. dental tissue. The language dental tissue and restorative material will be used for discussion purposes below but this should no way be construed as a limitation of this aspect of the invention to dental tissue but is being made merely for ease of discussion. The percent penetration of a treated zone can be that percent of the distance from the top of the zone to the bottom of the zone which is infiltrated by the restorative material. For example, the tissue infiltrating primer formulations of the present invention can provide greater than 25% penetration of restorative material into a treated zone of a dental tissue, at least about 50% penetration of restorative material into the treated zone of a dental tissue, at least about 75%, at least about 80%, at least about 90%, at least about 95%, or most preferably 100% penetration of a restorative material into treated zone of the dental tissue.

The treated zone of a target substrate, e.g. dental tissue, is intended to include that zone subjected to a pretreatment step. Pretreatment steps of target substrates of the present invention are art recognized and include such things as acid etching, laser etching, roughening, or any treatment which alters the physical and/or chemical nature of a target substrate.

Pretreatment steps for dental tissues are art recognized and typically include acid etching. Acid etching can be carried out with a variety of acids, including phosphoric, maleic, citric and oxalic or other art-recognized acids.

Another way of measuring the ability of the tissue infiltrating primer formulations of the present invention to facilitate penetration of a biomaterial is to determine the depth of penetration of the restorative material into the treated zone of a target substrate. The depth can be measured from the top of the treated zone. The primer formulations of the present invention are capable of facilitating penetration of a biomaterial into a treated zone of the dental tissue to a depth of at least about 1 millimeter, at least about 50 microns, at least about 10 microns, at least about 5 microns, or at least about 4 microns, or a depth of more than 3 microns. The presently available primer formulations do not facilitate penetration of a restorative material to these depths.

Another way of measuring the ability of the tissue infiltrating primer formulations of the present invention to facilitate penetration of a biomaterial is to consider the depth of penetration of the restorative material into the treated zone of a target substrate in conjunction with either the ability to achieve this depth in a reproducible manner and/or the ability of achieving this depth with a user having less than ordinary skill in the art, e.g., a technician rather than a dentist. The language "to achieve this depth in a reproducible manner" is art-recognized terminology and is intended to include variances of less than about 20 percent, more preferably less than about 10 percent, even more preferably less than about 5 percent, most preferably less than about 1 percent when a particular primer formulation is used for a group containing at least ten teeth, more preferably fifteen teeth.

The present invention also pertains to restorative material containing dental tissues. The restorative material containing dental tissue contains restorative material penetrated through a treated zone as described above. The dental tissue can be dentin or enamel, or a tooth per se.

The present invention also pertains to packaged primer formulations for use with a tissue infiltrating agent or packaged TIAs of the invention containing instructions for using the TIA in the methods described herein or with primer formulations. The packaged primer formulation can be any primer formulation as described above packaged with instructions for using the agent with a TIA or in a method of the present invention. The packaged primer formulations even further can contain the TIA in the same package, in the same vial as the primer formulation or in a separate vial.

The invention is further illustrated by the following examples which in no way should be construed as being further limiting. The contents of all references, pending patent applications, issued patents (worldwide) and published patent applications, cited throughout this application are hereby incorporated by reference.

EXAMPLE 1

Preparation of Medical or Dental Primer Formulations

A. Control Primer A

The control primer is a component of a conventional dental resin composite system sold as Scotchbond Multi-Purpose by 3M Dental Products Division, St. Paul, Minn., U.S.A. (hereinafter SBMP).

B. Preparation of The Tissue Infiltrating Agent (TIA) Containing Formulations (Primer-TIA)

The TIA containing formulations were prepared by combining a selected TIA with a selected amount of the control primer in ratios being measured by volume. For example, a 4:1 primer-TIA contains four parts of the control primer combined with one part of the selected TIA by volume. For ease of discussion, the primers or formulations of this invention will be referred to as shown above with the specific primers and TIAs being used forming part of the designation, e.g., SBMP primer-DMSO (4:1), Kerr primer-DMSO (9:1).

The SBMP primer-DMSO (9:1) TIA containing formulation was prepared as described below. Five (5) drops of SBMP primer were placed in a dispensing well (supplied as part of the SBMP kit). An aliquot (90 $\mu$l) of SBMP primer was withdrawn from the dispensing well and placed in a second well. An aliquot of DMSO (10 $\mu$l) was added to the second well forming a combined solution. The combined solution was then withdrawn and dispensed into a dispensing well twelve times to ensure adequate dispersion of the DMSO in the primer forming the TIA containing formulation (SBMP primer-DMSO (9:1)). The TIA containing formulation was then brushed onto the etched dentin surface using a disposable brush (supplied with the SBMP kit). The other TIA containing formulations described herein were prepared in a similar manner with modifications being made if the ratio of primer to TIA differed or the type of TIA or primer resin differed.

EXAMPLE 2
Demonstration that the Presence of a Tissue Infiltrating Agent in the Formulation Does Not Effect the Mechanical Bond of the Bonding Agent Ten bovine teeth (with their pulp chambers filled with water soaked sponges) for each group were embedded in methyl methacrylate and the surface of each tooth was ground into the dentin just below the dento-enamel junction. The final abrasive used on the dentin was water irrigated #600 grit SiC paper. The dentin was then etched with aqueous 10% maleic acid for fifteen seconds followed by washing with running water for thirty seconds. The dentin was gently dried but not desiccated with a stream of compressed air and two coats of a control primer (SBMP primer) or a primer of the present invention (the control primer combined with DMSO as a tissue infiltrating agent (hereinafter TIA) was applied to the etched dentin using a disposable brush as described above. The surface being primed was thoroughly wetted with two coats of the primer. Gentle drying with air after application of each primer coat produced a shiny surface on the dentin. The coated teeth were placed in a jig which held a gelatin capsule (no. 5 gelatin capsule having an internal diameter of 4.33 mm cut to a height of 3 mm) in place on the prepared dentin surface until adhesive resin (sold by 3M Dental Products Division, St. Paul, Minn., U.S.A. as a component of the SBMP kit) was placed inside the capsule and light-cured. The capsule was filled to the top with Z100 composite resin (sold by 3M Dental Products Division, St. Paul, Minn., U.S.A. as a component of the SBMP kit), after which the cylinder was light-cured from above for sixty seconds and from the sides for an additional sixty seconds. The samples were then stored in distilled water for twenty four hours and then shear tested on an Instron Universal Testing machine using conventional techniques. The teeth were fractured in liquid nitrogen, fixed and dehydrated in 100% alcohol for Critical Point Drying (CPD) and finally sputter coated with 3 nm of platinum for assessing and documentation under SEM (Titley et al., Am J Dent 1994:7 190–194). A ratio of 9:1 (primer:TIA) gave the highest bond strength and statistically the addition of the TIA did not detrimentally effect the mechanical bond of the original bonding agents (see Table 2).

TABLE 2

| FORMULATION | RATIO OF PRIMER TO TISSUE INFILTRATING AGENT | MEAN MECHANICAL SHEAR BOND STRENGTH FOR GROUP (MPA) |
| --- | --- | --- |
| SBMP primer | | 15.54 ± 6.97 |
| SBMP primer-DMSO | (4:1) | 17.09 ± 8.46 |
| SBMP primer-DMSO | (9:1) | 21.51 ± 5.81 |
| SBMP primer-DMSO | (9.8:0.2) | 19.97 ± 5.33 |

Figure 2A:
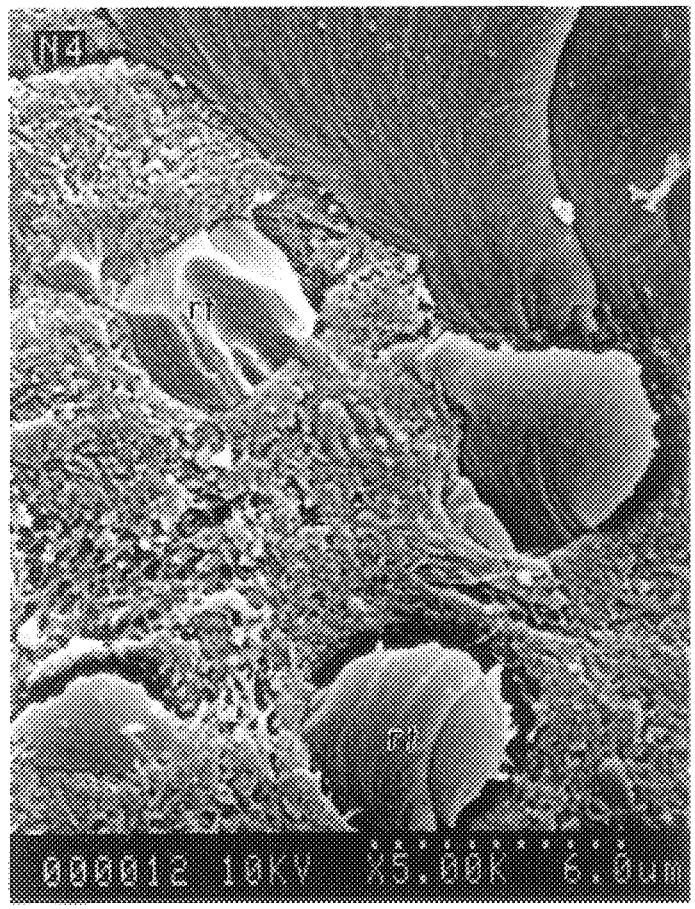
FIG. 2A is a SEM of a top view of dentin in a tooth that shows the degree of enhanced integration of resin within the residual collagen layer of dentin (following an acid etch treatment with 10% maleic acid and priming with TIA). This integration is achieved with the use of a SBMP primer and dimethylsulphoxide (DMSO) (9:1) formulation. The figure shows the continuity of resin located in the tubules with resin that is able to infiltrate collagen tissue. Fifty percent or greater of the perimeter of the resin tags are fused with the resin penetrated collagen.
Figure 2B:
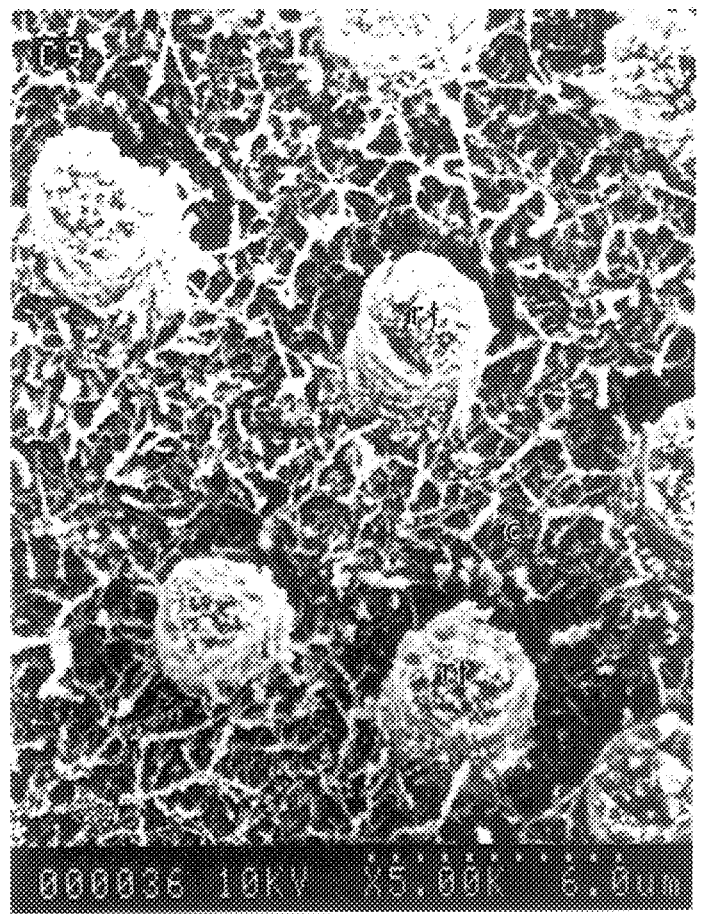
FIG. 2B is a SEM from the control sample of Example 2 (SBMP primer).

FIGS. 2A and 2B compare the degree of integration of resin within the residual collagen layer when using the control (2B) or the SBMP primer DMSO (9:1) (2A) formulations.

Figure 3:
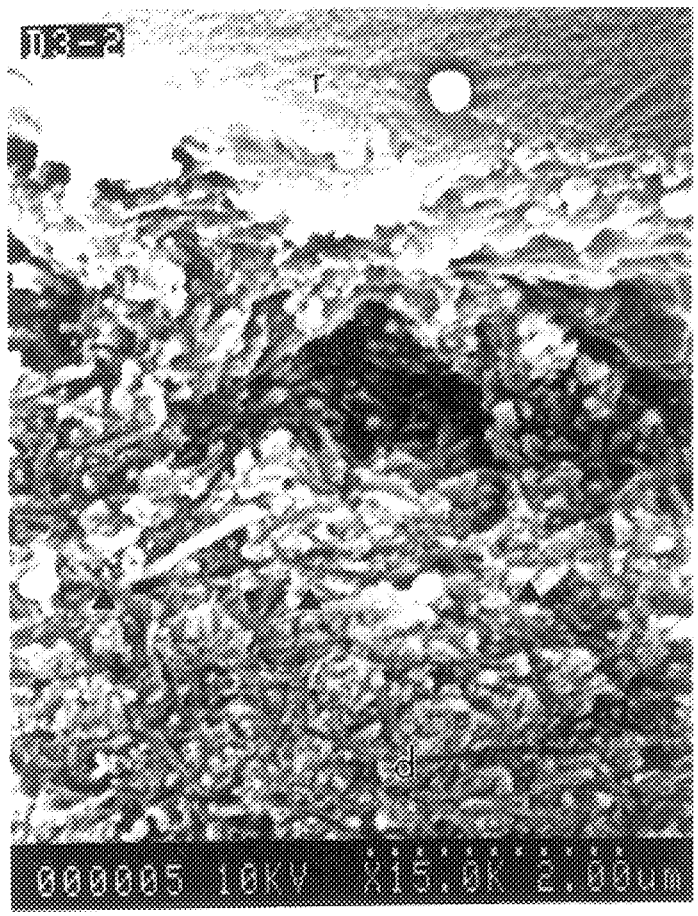
FIG. 3 is an SEM that shows a profile of a freeze fractured dentin zone in a tooth that was prepared with SBMP primer-DMSO (9:1) as described in Example 3. This close up view of the cross-section shows a continuity of resin from the unfilled resin layer at the top of the photo through the etched dentin and down to the sound dentin. It can be seen that the residual resin actually molded the area where collagen fibrils once were present.
Figure 4A:
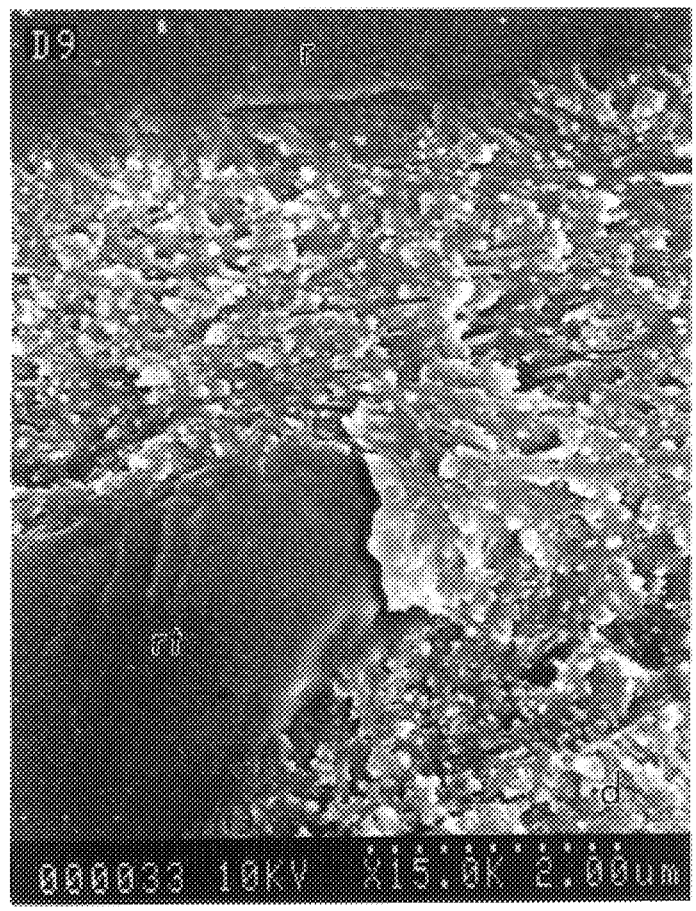
FIG. 4A is an SEM that shows that a sample treated with SBMP primer-DMSO (9:1) as described in Example 3 showed a continuity of resin with both the unfilled resin located at the top of the dentin surface as well as with resin tags located as deep as 4 microns from the upper surface. In this photo, the resin tag penetrates the dentin below the demineralized zone.
Figure 4B:
FIG. 4B is an SEM that shows that a sample treated with the SBMP primer (control) as described in Example 3 did not show continuity of the unfilled resin layer with the collagen matrix. A gap exists between unfilled resin and the etched zone of the dentin indicating the absence of complete penetration of resin within the collagen matrix of the etched zone.

EXAMPLE 3
Demonstration of the Effect of A Tissue Infiltrating Agent on the Penetration of A Composite Resin Into A Collagen Matrix Fifteen bovine teeth (with their pulp chambers filled with water soaked sponges) for each group were embedded in methyl methacrylate and the surface was ground into the dentin just below the dento-enamel junction. The final abrasive used on the dentin was water irrigated #600 grit SiC paper. The dentin was then etched with aqueous 10% maleic acid for fifteen seconds followed by washing with running water for thirty seconds. The dentin was gently dried but not desiccated with a stream of compressed air and two coats of the SBMP primer or a primer-TIA of this invention was applied to the etched dentin. Gentle drying with a stream of compressed air after application of each primer coat produced a shiny surface on the dentin and an adhesive resin (sold by 3M Dental Products Division, St. Paul, Minn., U.S.A. as a component of the SBMP kit) was placed on the primed surface. The samples were then stored in distilled water for twenty four hours. All teeth were then freeze fractured in liquid nitrogen, fixed and dehydrated in 100% alcohol for the critical point drying (CPD) process and finally sputter coated with 3 nm of platinum for assessing and documentation under SEM. The results indicating the degree of resin penetration are shown in the SEMs of FIGS. 3, 4A and 4B which are described above.

EXAMPLE 4
Demonstration Of The Effect of A Tissue Infiltrating Agent on Bonding To Enamel Fifteen bovine teeth for each group were embedded in methyl methacrylate and the enamel surface flattened with water irrigated #600 grit SiC paper. The enamel was then etched with aqueous 35% phosphoric acid for fifteen seconds followed by washing in running water for thirty seconds. The etched enamel was gently dried with a stream of compressed air and one coat of the SBMP primer or primer of the present invention (SBMP primer-DMSO (9:1)) was applied to the surface. Gentle drying with compressed air after primer coat application produced a shiny surface on the enamel. The coated teeth were placed in a jig which held a gelatin capsule (no. 5 gelatin capsule having an internal diameter of 4.33 mm cut to a height of 3 mm) in place until adhesive resin (sold by 3M Dental Products Division, St. Paul, Minn., U.S.A. as a component of the SBMP kit) was placed inside the capsule and light cured. The capsule was filled to the top with Z100 composite resin (sold by 3M Dental Products Division, St. Paul, Minn., U.S.A. as a component of the SBMP kit), after which the cylinder was light cured from above for sixty seconds and from the sides for an additional sixty seconds. The samples were then stored in distilled water for twenty four hours and then shear tested on an Instron Universal Testing Machine using conventional techniques. The ratio of 9:1 (primer:TIA) gave the higher bond strength and the addition of the TIA did not detrimentally effect the mechanical bond of the original bonding agents (see Table 3).

TABLE 3

| FORMULATION | MEAN MECHANICAL SHEAR BOND STRENGTH |
| --- | --- |
| SBMP primer | 18.83 ± 3.38 |
| SBMP primer-DMSO (9:1) | 19.64 ± 4.41 |

EXAMPLE 5
Demonstration of the Effect of A Tissue Infiltrating Agent on the Penetration of Resin Into A Collagen Matrix After Etching with 35% Phosphoric Acid (Two Coats of Primer)

Figure 5:
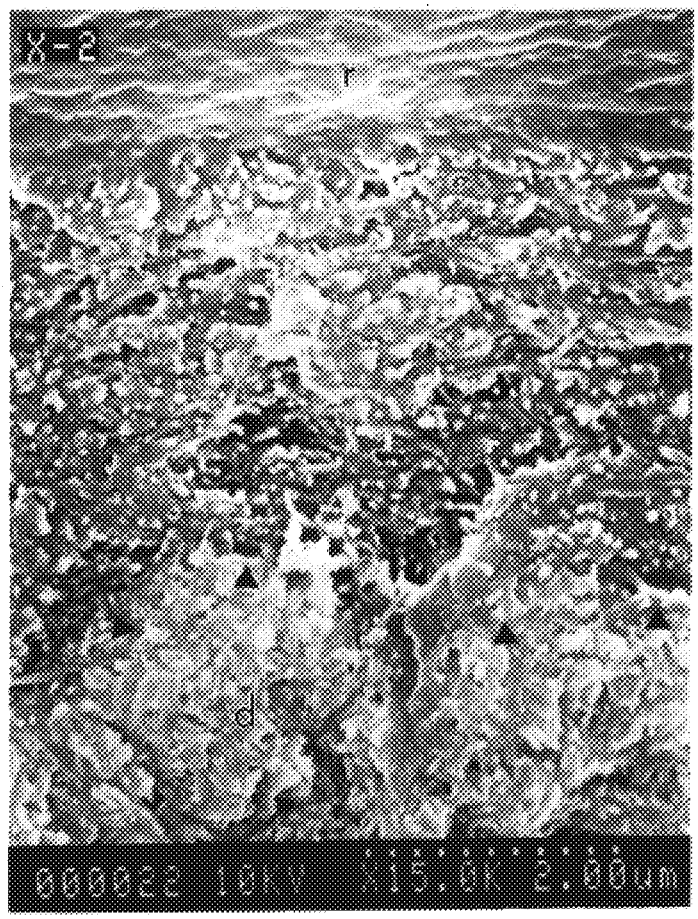
FIG. 5 shows complete infiltration of the acid etched zone by the resin when TIA is applied with the primer and therefore demonstrates the potential application of TIA with various etchant formulations (see Example 5). Alternate etchant formulations (e.g., 35% phosphoric acid) remove more mineral material than do 10% maleic acid solutions and further accentuate the degree of penetration achieved with the TIA, DMSO. There is complete continuity of the resin from the unfilled resin layer at the top to the sound dentin layer below the etched layer. This continuous layer of cured resin effectively acts as a support for the collagen matrix, following the removal of the rigid mineral by acid etching.

Fifteen bovine teeth (with their pulp chambers filled with water soaked sponges) for each group were embedded in methyl methacrylate and the surface was ground into the dentin just below the dento-enamel junction. The final abrasive used on the dentin was water irrigated #600 grit SiC paper. The dentin was then etched with aqueous 35% phosphoric acid for fifteen seconds followed by washing in running water for thirty seconds for the SBMP primer-DMSO (9:1) formulation. The dentin was gently dried but not desiccated with a stream of compressed air and two coats of the SBMP primer-DMSO (9:1) was applied to the etched dentin. Gentle drying with a stream of compressed air after each primer coat produced a shiny surface on the dentin and adhesive resin was photocured on the primed surface. The samples were then stored in distilled water for twenty four hours. All teeth were subsequently freeze fractured in liquid nitrogen, fixed and dehydrated in 100% alcohol for the critical point drying (CPD) process and finally sputter coated with 3 nm of platinum for assessing and documentation under SEM. The results indicating the degree of resin penetration are shown in the SEM of FIGS. 5 as described above.

EXAMPLE 6
Demonstration of the Effect of DMSO on the Penetration of Resin Into A Collagen Matrix After Etching With 35% Phosphoric Acid (One Coat of Primer)

Figure 6A:
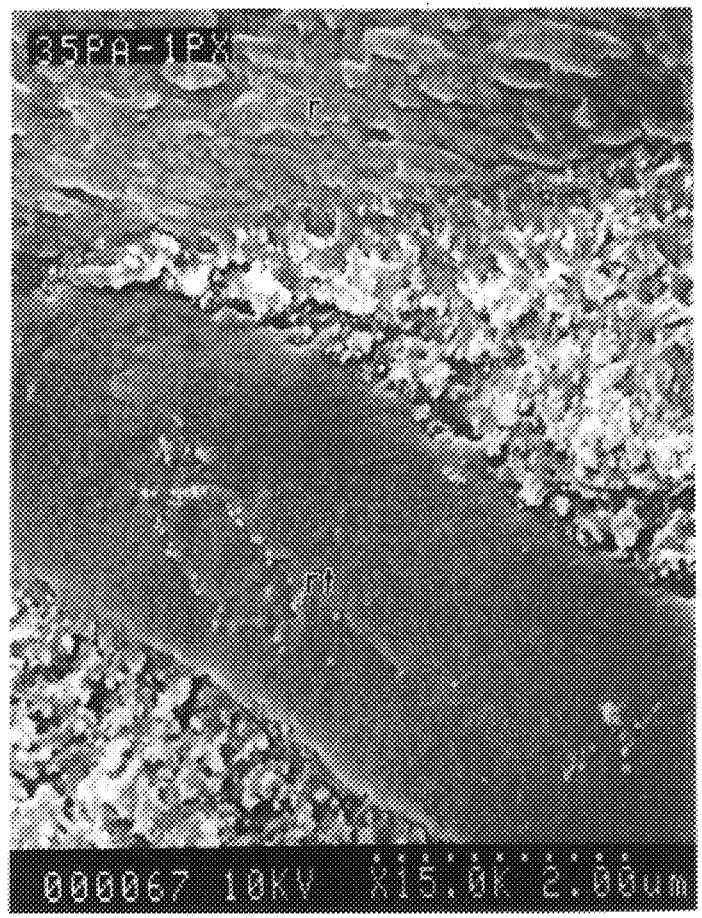
FIGS. 6A and 6B show cross-sectional views of dentin after treatment with 35% phosphoric acid and one coat of TIA/primer mixture followed by the adhesive resin application. One single coat of TIA treated primer was applied to the test samples to demonstrate the minimal amount of TIA primer applications that were sufficient to achieve an effective penetration of resin into the collagen matrix of etched dentin.
Figure 6B:
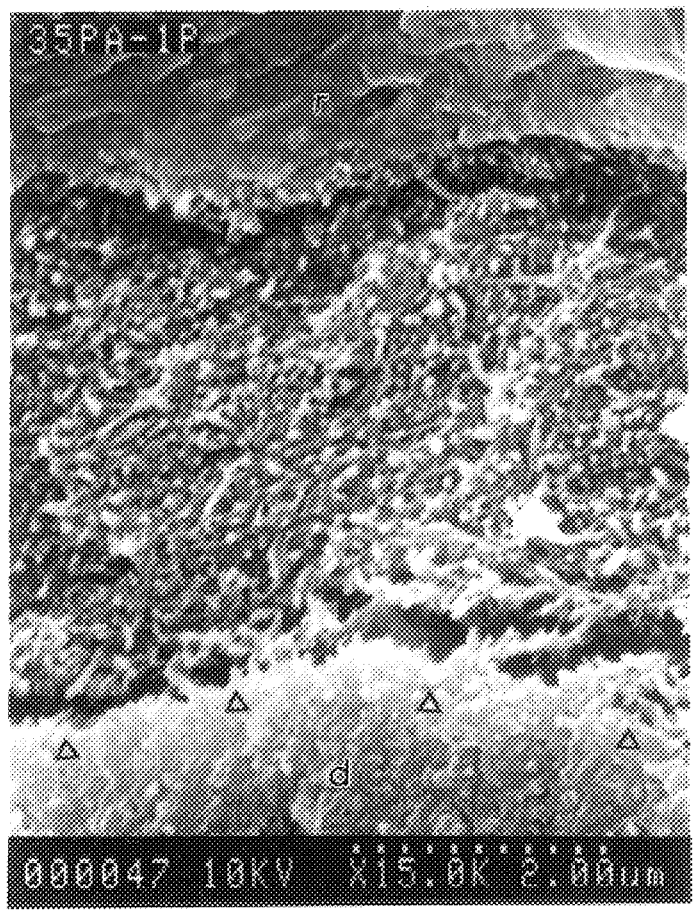

Fifteen bovine teeth (with their pulp chambers filled with water soaked sponges) for each group were embedded in methyl methacrylate and the surface was ground into the dentin just below the dento-enamel junction. The final abrasive used on the dentin was water irrigated #600 grit SiC paper. The dentin was then etched with aqueous 35% phosphoric acid for fifteen seconds followed by washing in running water for thirty seconds. The dentin was gently dried but not desiccated with a stream of compressed air and one coat of the control primer (SBMP primer) or the TIA containing primer of this invention was applied to the etched dentin, gentle drying with a stream of compressed air after the primer coat produced a shiny surface on the dentin and an adhesive resin was placed on the primed surface and light cured. The samples were then stored in distilled water for twenty four hours. All teeth were then freeze fractured in liquid nitrogen, fixed and dehydrated in 100% alcohol for the critical point drying (CPD) process and finally sputter coated with 3 nm of platinum for assessing and documentation under SEM. The results indicating the degree of resin penetration are shown in the SEMs of FIGS. 6A and 6B as described above.

EXAMPLE 7
Comparison Between Common Solvents and Tissue Infiltrating Agents of the Present Invention This example shows that an amide (dimethyl formamide) and an alcohol (methanol) did not perform as effective TIAs of the present invention.

Figure 7A:
FIG. 7A is an SEM showing that resin flowed into the dentinal tubule but failed to penetrate the collagen layer with the use of methanol (primer:methanol ratio 9:1) rather than DMSO in a formulation of the present invention (see Example 7).
Figure 7B:
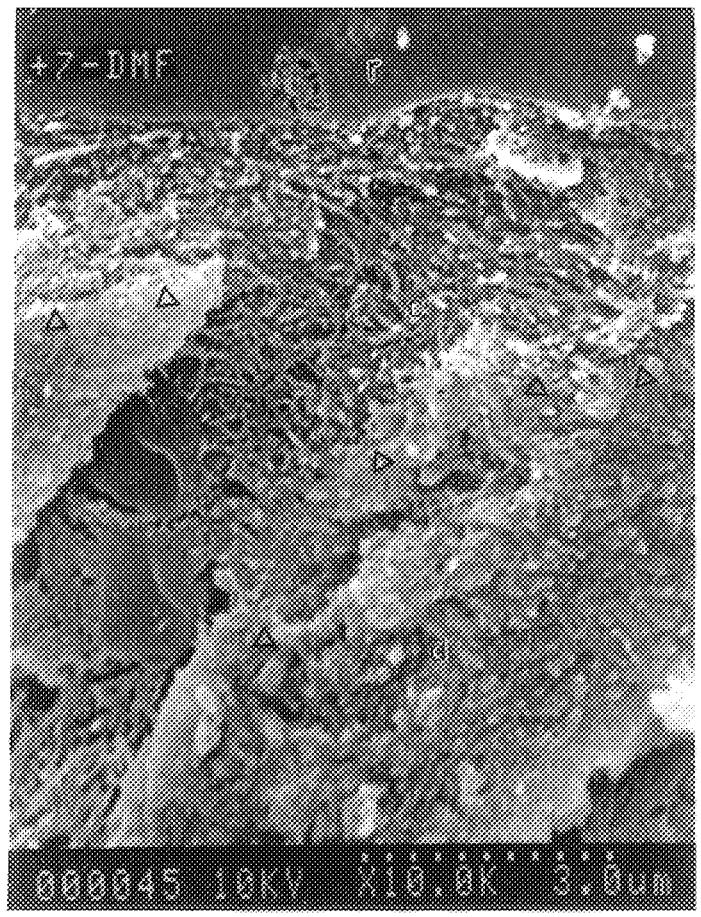
FIG. 7B is an SEM showing that some resin flowed into the dentinal tubule but it failed to penetrate the collagen layer with the use of N,N-dimethylformamide (DMF) (primer:DMF ratio 9:1) in a formulation of the present invention (see Example 7).

A total of six bovine teeth were ground to just below the dentinal enamel junction (DEJ) with water irrigated SiC paper with a final grit size #600. All of the teeth were acid etched with a 35% phosphoric acid for fifteen seconds and washed in running water for sixty seconds. The teeth were divided into three groups and processed as follows:
1. Control (2 teeth) one coat of SBMP primer, Unfilled Bonding Resin (UBR) photocured
2. Methanol Group—(2 teeth) SBMP primer and HPLC grade methanol (ratio 9:1/primer, one coat of UBR photocured
3. N,N-dimethyl formamide (DMF) Group—(2 teeth) SBMP primer and HPLC Grade DMF (ratio 9:1/primer:DMF), one coat of primer, UBR photocured All teeth were then freeze fractured in liquid nitrogen, fixed and dehydrated in 100% alcohol for the critical point drying (CPD) process and finally sputter coated with 3 nm of platinum for assessing and documentation under SEM. As shown in FIGS. 7A (methanol) and 7B (DMF), methanol and DMF failed to assist penetration of the collagen layer at a 9:1 ratio of primer to solvent.

EXAMPLE 8
Demonstration of the Effect of DMAC on the Penetration of Resin Into A Collagen Matrix A total of six bovine teeth (with their pulp chambers filled with water soaked sponges) were ground to just below the dentinal enamel junction (DEJ) with water irrigated SiC paper with a final grit size of #600. All teeth were acid etched with a 35% phosphoric acid gel for fifteen seconds and washed in running water for sixty seconds. The teeth were divided into three groups and processed as follows:

Group I—the DMAC was added to the SBMP primer at a ratio of 9:1 (primer/DMAC) and one coat was applied to the dentin surface followed by the Unfilled Bonding Resin (UBR) which was then photocured.

Group II—the DMAC was added to the SBMP primer at a ratio of 9.5:0.5 (primer/DMAC) and one coat was applied to the dentin surface followed by the Unfilled Bonding Resin (UBR) which was then photocured.

Group III—the DMAC was added to the SBMP at a ratio of 4:1 (primer/DMAC) and one coat was applied to the dentin surface followed by the Unfilled Bonding Resin (UBR) which was then photocured.

Figure 8A:
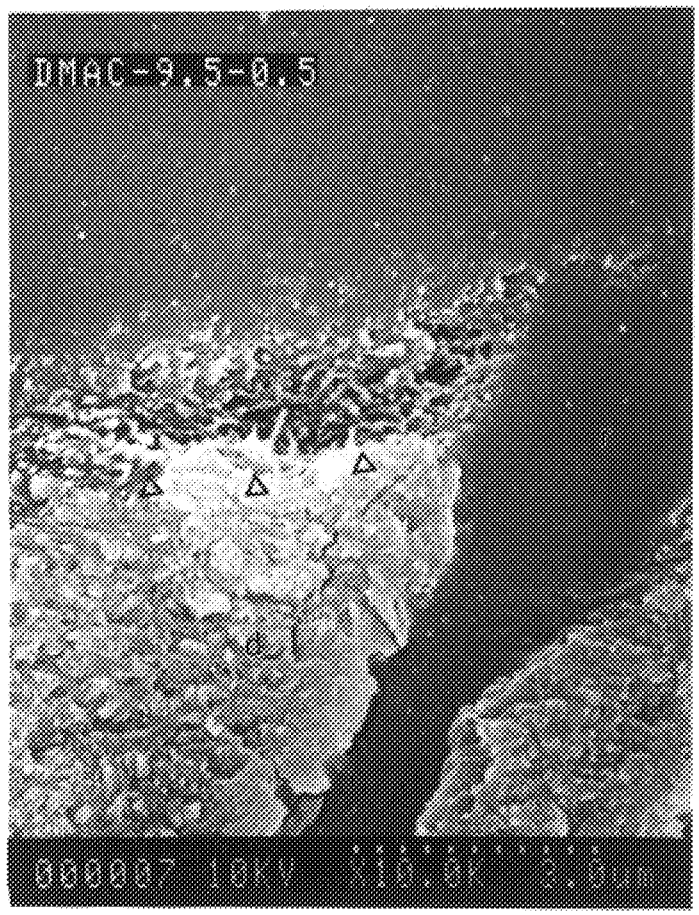
FIG. 8A is an SEM showing that N,N-dimethylacetamide (DMAC) at a ratio by volume (primer:TIA) of 9.5:0.5 did not aid in the penetration of the resin into the collagen layer (see Example 8).
Figure 8B:
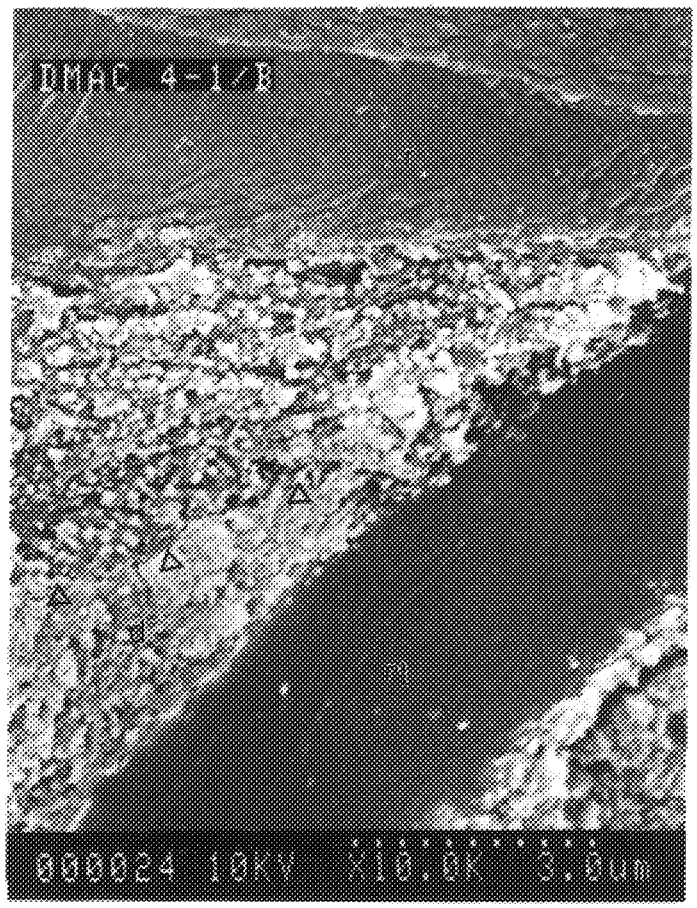
FIG. 8B is an SEM showing that DMAC at a ratio by volume (primer:TIA) of 4:1 aided in the partial penetration of resin into the collagen layer (see Example 8).
Figure 8C:
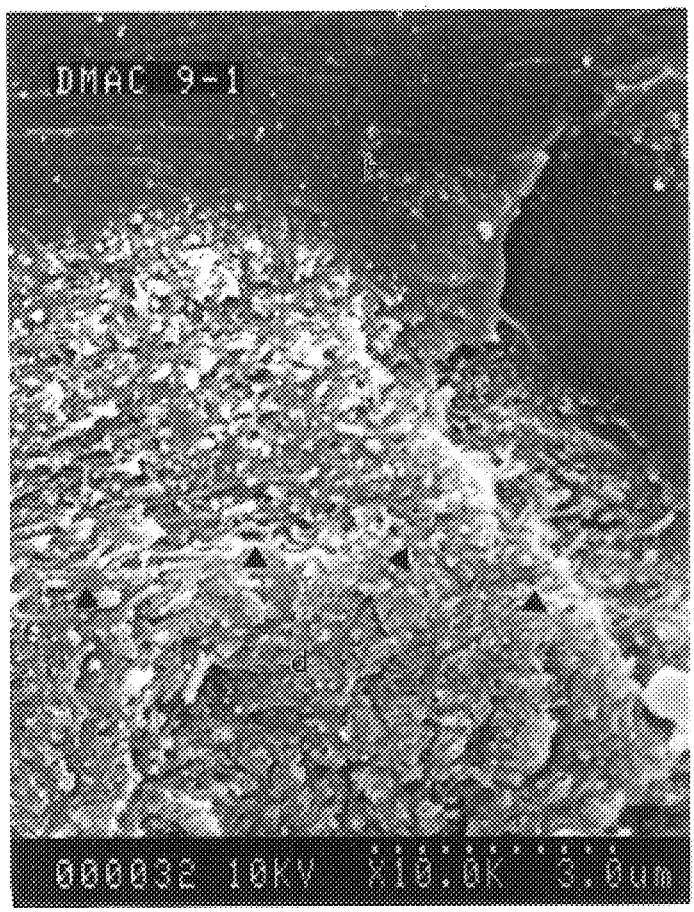
FIG. 8C is an SEM showing that DMAC at a ratio of 9:1 aided in the penetration of the adhesive resin into the collagen layer (see Example 8).

All teeth were then freeze fractured in liquid nitrogen, fixed and dehydrated in 100% alcohol for CPD processing and finally sputter coated with 3 nm of platinum for assessing and documentation under SEM. FIGS. 8A shows poor resin infiltration near a resin tag for a primer/DMAC ratio of 9.5:0.5. FIG. 8B shows that at a ratio of 4:1 there was partial penetration of the resin into the collagen layer. FIG. 8C shows complete infiltration of the collagen layer with the adhesive resin at a ratio of 9:1.

EXAMPLE 9
Demonstration of the Effect of a Tissue Infiltrating Agent on Penetration Using A Second Dentin Bonding System This example demonstrates that DMSO also aids penetration when used with a different dentin bonding system (Optibond dual cure sold by Kerr Manufacturing Co., Romulus, Mich. 48174,U.S.A.). The Kerr product uses a photocured primer on the dentin prior to placement of a light-cured adhesive resin.

Fifteen bovine teeth (with their pulp chambers filled with water soaked sponges) were embedded in methyl methacrylate and the buccal surface ground to just below the dentinal enamel junction using water irrigated SiC paper. The test dentinal surface was prepared with water irrigated #600 grit SiC paper. The prepared test dentinal surface was then acid etched with 35% phosphoric acid gel for fifteen seconds and washed with running water for sixty seconds. The etched dentin was gently dried but not dessicated with a stream of compressed air. The Optibond primer was then immediately placed on the dentin surface, gently blown dry with a stream of compressed air and then light cured for twenty seconds. The embedded tooth was then mounted on a jig for placement of a gelatin cylinder of a known diameter and surface area. The Optibond bonding resin paste and catalyst liquid were dispensed and mixed for twenty seconds after which this material was placed within the confines of the gelatin cylinder as a single layer over the primed dentin. This adhesive bonding resin layer was then light-cured for thirty seconds. A composite resin (Z 100) was added to the gelatin cylinder filling it to the rim and light cured from above for sixty seconds and the sides for sixty seconds. The samples were then stored in distilled water for twenty four hours.

Figure 9A:
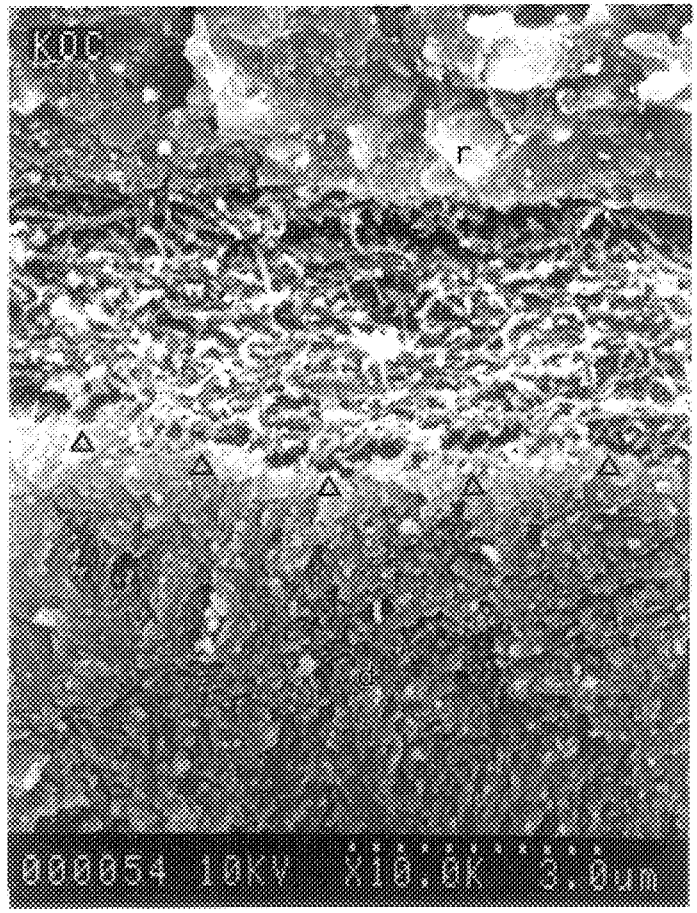
FIGS. 9A and 9B are SEMs showing that DMSO also aids penetration when used with a different dentin bonding system (Optibond dual cure sold by Kerr Manufacturing Co- see Example 9).
Figure 9B:

A total of fifteen bovine teeth were processed in the same manner as described above for the control group except that DMSO was added as a TIA to the primer at a ratio of 9:1 (primer/TIA). After twenty four hours, both groups were shear tested on an Instron Universal Testing Machine. All teeth were then freeze fractured in liquid nitrogen, fixed and dehydrated in 100% alcohol for CPD processing and finally sputter coated with 3 nm of platinum for assessing and documentation under SEM. The results indicating the degree of resin penetration are shown in the SEMs of FIGS. 9A (control) and 9B. The SEM of FIG. 9B shows that the primer completely penetrated the collagen matrix.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

We claim:

1. A dental tissue infiltrating primer formulation, comprising:
an effective amount of a tissue infiltrating agent; and
a primer forming a tissue infiltrating primer formulation, the tissue infiltrating primer formulation when applied to a treated dental tissue providing a farther barrier seal to microleakage by enhancing restorative material penetration into the dental tissue when compared to the distance of a barrier seal achieved with any non-tissue infiltrating primer formulation, wherein the tissue infiltrating agent is a compound within one of the following formulae:

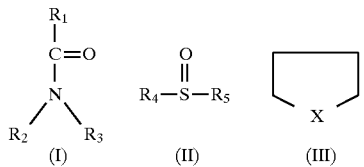

wherein $R_1$–$R_5$ are each independently selected from the group consisting of hydrogen, alkyl, alkenyl, alkynyl, alkoxyl and haloalkyl; and X is selected from the group consisting of O, S and —$SO_2$—.

2. The formulation of claim 1 wherein the tissue infiltrating agent is dimethylsulphoxide and the primer is a Scotchbond Multi-Purpose primer.

3. The formulation of claim 2 containing one part by weight of tissue infiltrating agent to nine parts by weight of the primer.

4. A dental tissue infiltrating primer formulation, comprising:
an effective amount of a tissue infiltrating agent; and
a primer forming a tissue infiltrating primer formulation, the tissue infiltrating primer formulation when applied to a treated dental tissue providing a farther barrier seal to microleakage by enhancing restorative material penetration into the dental tissue when compared to the distance of a barrier seal achieved with any non-tissue infiltrating primer formulation, wherein the tissue infiltrating agent is selected from the group consisting of dimethylsulphoxide, dimethylacetamide, dimethylformamide, and tetrahydrofuran, N-methylpyrrolidinone, tetrahydrothiophene, 2-methyl tetrahydrofuran, 1,4-dioxane, sulfolane, and nitromethane.

5. A dental tissue infiltrating primer formulation, comprising:
an effective amount of a tissue infiltrating agent; and
a primer forming a tissue infiltrating primer formulation, the tissue infiltrating primer formulation when applied to a treated dental tissue providing a farther barrier seal to microleakage by enhancing restorative material penetration into the dental tissue when compared to the distance of a barrier seal achieved with any non-tissue infiltrating primer formulation, wherein the dipole moment of the tissue infiltration agent is at least 2.00 or the dielectric constant of the tissue infiltration agent is at least 40.

6. A dental tissue infiltrating primer formulation, comprising:
an effective amount of a tissue infiltrating agent; and
a primer forming a tissue infiltrating primer formulation, the tissue infiltrating primer formulation providing greater than twenty five percent penetration of a restorative material into a treated zone of a dental tissue.

7. The dental tissue infiltrating primer formulation of claim 6 wherein the tissue infiltrating primer formulation provides at least about fifty percent penetration of a restorative material into the treated zone of a dental tissue.

8. The dental tissue infiltrating primer formulation of claim 7 wherein the tissue infiltrating primer formulation provides at least about seventy five percent penetration of a restorative material into the treated zone of a dental tissue.

9. The dental tissue infiltrating primer formulation of claim 8 wherein the tissue infiltrating primer formulation provides at least about eighty percent penetration of a restorative material into the treated zone of a dental tissue.

10. The dental tissue infiltrating primer formulation of claim 9 wherein the tissue infiltrating primer formulation provides at least about ninety percent penetration of a restorative material into the treated zone of a dental tissue.

11. The dental tissue infiltrating primer formulation of claim 10 wherein the tissue infiltrating primer formulation provides at least about ninety five percent penetration of a restorative material into the treated zone of a dental tissue.

12. A dental tissue infiltrating primer formulation, comprising:
an effective amount of a tissue infiltrating agent; and
a primer forming a tissue infiltrating primer formulation, the tissue infiltrating primer formulation capable of providing penetration of a restorative material into the treated zone of a dental tissue to a depth of at least about one millimeter.

* * * * *